US008883164B2

(12) United States Patent
Ponniah et al.

(10) Patent No.: US 8,883,164 B2
(45) Date of Patent: Nov. 11, 2014

(54) TARGETED IDENTIFICATION OF IMMUNOGENIC PEPTIDES

(75) Inventors: Sathibalan Ponniah, Columbia, MD (US); George E. Peoples, Fulton, MD (US); Catherine E. Storrer, Columbia, MD (US); Michael Flora, Mt. Airy, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 13/336,068

(22) Filed: Dec. 23, 2011

(65) Prior Publication Data

US 2012/0107311 A1 May 3, 2012

Related U.S. Application Data

(60) Division of application No. 12/045,402, filed on Mar. 10, 2008, which is a continuation of application No. PCT/US2006/035171, filed on Sep. 8, 2006.

(60) Provisional application No. 60/714,865, filed on Sep. 8, 2005.

(51) Int. Cl.
*A61K 39/00* (2006.01)
*A61K 39/395* (2006.01)

(52) U.S. Cl.
USPC ..................................... 424/185.1; 424/143.1

(58) Field of Classification Search
None
See application file for complete search history.

(56) References Cited

U.S. PATENT DOCUMENTS

| | | |
|---|---|---|
| 4,433,092 A | 2/1984 | Nemeth |
| 4,554,101 A | 11/1985 | Hopp |
| 4,631,211 A | 12/1986 | Houghten |
| 4,631,221 A | 12/1986 | Disselbeck et al. |
| 4,708,781 A | 11/1987 | Poorten |
| 4,708,871 A | 11/1987 | Geysen |
| 4,833,092 A | 5/1989 | Geysen |
| 5,194,392 A | 3/1993 | Geysen |
| 5,480,971 A | 1/1996 | Houghton et al. |
| 5,550,214 A | 8/1996 | Eberlein et al. |
| 5,726,023 A | 3/1998 | Cheever et al. |
| 6,075,122 A | 6/2000 | Cheever et al. |
| 6,127,524 A | 10/2000 | Casipit et al. |
| 6,338,945 B1 | 1/2002 | Nicolette |
| 6,780,598 B1 | 8/2004 | Kokolus |
| 7,179,645 B2 | 2/2007 | Humphreys et al. |
| 7,252,829 B1 | 8/2007 | Sette et al. |
| 7,446,185 B2 | 11/2008 | Nelson |
| 2003/0096298 A1 | 5/2003 | Barnea et al. |
| 2004/0018971 A1 | 1/2004 | Fikes et al. |
| 2005/0119288 A1* | 6/2005 | Bhattacharya et al. .... 514/266.2 |
| 2005/0169934 A1 | 8/2005 | Ioannides et al. |
| 2010/0209443 A1 | 8/2010 | Peoples et al. |

FOREIGN PATENT DOCUMENTS

| | | |
|---|---|---|
| WO | 9420127 | 9/1994 |
| WO | 0136452 | 5/2001 |
| WO | 2005007694 | 1/2005 |
| WO | 2005/076975 | 8/2005 |

OTHER PUBLICATIONS

Murray et al (Clinical Cancer Research, 2002, 8:3407-3418).*
Kono et al (Clinical Cancer Research, 2004, 10:2538-2544, published online Apr. 8, 2004).*
zum Buschenfelde et al (Cancer Research, 2002, 62:2244-2247, IDS).*
Capizzi (Investigational New Drugs, 1996, 14:249-256).*
Rongcun et al., "Identification of new her-2/neu-derived peptide epitopes that can elicit specific ctl against autologous and allogeneic carcinomas and melanomas," J. Immunol., 153:1037-1044, 1999.
Roy and Nicholson, "Cross-talk in cell death signaling," J. Exp. Med., F21-25, 2000.
Saper et al., "Refined structure of the human histocompatibility antigen hla-a2 at 2•6 Åresolution," J. Mol. Biol., 219:277, 1999.
Simon et al., "Modeling mhc class II molecules and their bound peptides as expressed at the cell surface;" Mol. Immunol., 38(9):651-687, 2002.
Spencer and Braciale, "Incoomplete cd8+ t lymphocyte differentiation as a mechanism subdominant cytotoxic t lymphocyte responses to a viral antigen," J. Exp. Med., 191:1687-1698, 2000.
Stern and Wily, "Antigenic peptide binding by class I and class II histocompatiblitty proteins," Structure, 2:245-251, 1994.
Thomas et al., "The structure: metabolism and function of the carcinoembryonic antigen gene family," Biochim. Biophys. Acta., 1032:177, 1990.
Van der Zee et al., "Efficient mapping and characterization of a t cell epitope by the simultaneous synthesis of multiple peptides," Eur. J. Immunol., 10:43-47, 1989.
Wallace et al., "Mechanisms of adoptive immunotherapy: improved methods for in vivo tracking of tumor-infiltrating lymphocytes and lymphokine-activated killer cells," Cancer Res., 63:2358-2367, 1993.
Ward et al., "Oxidant-induced s-glutathiolation inactivates protein kinase c-α (pkc-α): a potential mechanism of pkc isozyme sozyme regulation," Biochemistry, 39:10319, 2000.
Warner et al, "Induction of HIV-specific ctl and antibody responses in mice using retroviral vector-transduced cells," AIDS Res. and Human Retroviruses, 7:645-655, 1991.
Weidmann et al., "Relevance of the t cell for immunotherapy of cancer," Cancer Immunol. Immunother., 39:1-14, 1994.

(Continued)

*Primary Examiner* — Laura B Goddard
(74) *Attorney, Agent, or Firm* — MH2 Technology Law Group, LLP

(57) ABSTRACT

This invention relates generally to identifying peptide sequences involved in antibody binding to any protein for synthesis of vaccine treatments. This novel method allows for a more manageable vaccine peptide discovery and specific generation of unique immunogenic peptides from self-tumor associated proteins and/or foreign proteins from infectious organisms for specific and/or enhanced expression only in the presence of the antibody.

9 Claims, 8 Drawing Sheets

(56) References Cited

OTHER PUBLICATIONS

Weinberger et al., "Identification of human glucocorticoid receptor complementary dna clones by epitope selection," Science, 228:740-742, 1985.
Williams et al., "A kinetic threshold between negative and positive selection based on the longetivity of the t cell receptor-ligand complex," J. Exp. Med., 189:1531-1544, 1999.
Wolf et al., "An integrated family of amino acid sequence analysis programs," Comput. Appl. Biosci., 4(1):187-191, 1988.
Zaks and Rosenberg, "Immunization with a peptide epitope (p. 369-377) from her-2/neu leads to peptide-specific cytotoxic t lymphocytes that fail to recognize her-2/neu+ tumors," Cancer Res., 68:4902-4908, 1998.
zum Buschenfelde et al., "Generation of tumor-reactive ctl against the tumor-associated antigen her2 using retrovirally transduced dentritic cells derived from cd34+ hemopoietic progenitor cells," J. Immunol., 165:4133-4140, 2000.
Lara, Primo N. et al., "Trastuzumab Plus Docetaxel in HER-2/neu—Positive Prostate Carcinoma, Final Results from the Californica Cancer Consortium Screening and Phase II Trial," Cancer, May 15, 2004, vol. 100, No. 10, pp. 2125-2131.
zum Buschenfelde et al. (Cancer Research, 2002, 62:2244-2247).
Mittendorf et al. (Proc. Amer. Assoc. Cancer Research, Apr. 2005, 46; abstract #3449).
Hird et al., Journal of Surgical Research, Feb. 2008, vol. 144, No. 2, pp. 180-181.
Webster et al., Breast Cancer Research and Treatment, 2006. vol. 100, Supp. 1, pp. S79-S80.
Mittendorf et al., Journal of the American College of Surgeons, Sep. 2006, vol. 203, No. 3, p. S79.
Mittendorf et al., Annals of Surgical Oncology, Aug. 2006, vol. 13, No. 8, pp. 1085-1098.
Pero et al., British Journal of Cancer, May 2007, vol. 96, No. 10, pp. 1520-1525.
Knutson et al., The Journal of Clinical Investigation, Feb. 2001, vol. 107, No. 4, pp. 477-484.
Tanaka et al., International Journal of Cancer, Nov. 2011, vol. 94, No. 4, pp. 540-544.
Mittendorf et al., Breast Diseases: A Year Book Quarterly, Jan. 2007, vol. 17, No. 4, pp. 318-320.
International Search Report, International Application No. PCT/GB2008/050227, Oct. 17, 2008.
Fisk, Bryan et al., "Identification of an immunodominant Peptide of HER-2/neu Protooncogene Recognized by Ovarian Tumor-specific Cytotoxic T Lymphocyte Lines," J. Exp. Med., vol. 181, Jun. 1995, pp. 2109-2117.
Yao et al., "Identification of Parathyroid Hormone-related Protein-derived Peptides Immunogenic in HLA-A2 Positive Prostate Gland Cancer Patients," Proceedings of 63rd Annual Meeting of the Japanese Cancer Association, 2004, p. 295, P-0735 (with English translation).
English translation of Office Action dated Jun. 26, 2012 from Japanese Patent Application No. 2008-530244, 2 pages.
Communication dated May 21, 2013 from Canadian Application No. 2,622,036, pp. 1-4.
Non-Final Office Action dated Apr. 21, 2014 from U.S. Appl. No. 12/045,402, pp. 1-18.
Baxevanis et al., "Immunobiology of HER-2/neu oncoprotein and its potential application in cancer immunotherapy," Cancer Immunol. Immunother., 53(3):166-75, Mar. 2004. Epub Dec. 18, 2003.
Emens et al., "Augmenting the Potency of Breast Cancer Vaccines: Combined Modality Immunotherapy," Breast Dis., 20:13-24, 2004.
Non-Final Office Action dated Jun. 25, 2014 from U.S. Appl. No. 13/774,829, pp. 1-7.
Cruz et al., "Protein vaccination with the HER2/neu extracellular domain plus anti-HER2/neu antibody-cytokine fusion proteins induces a protective anti-HER2/neu immune response in mice," Vaccine, 21:1317-1326, 2003.
Supplementary European Search Report mailed Apr. 11, 2014 in European Application No. 06824918.4.

Knutson et al., "Tumor antigen-specific T helper cells in cancer immunity and immunotherapy", Cancer Immunol. Immunother., 54(8):721-728, Aug. 1, 2005.
Mittleman et al., "Monoclonal and polyclonal humoral immune response to EC HER-2/neu peptides with low similarity to the host's proteome", Int. J. Cancer., 98(5):741-747, Apr. 10, 2002.
Dakappagari, et al., "Prevention of mammary tumors with a chimeric HER-2 B-cell epitope peptide vaccine," Cancer Res., 60(14):3782-3789, Jul. 15, 2000.
Ramasamy et al., "Characterisation of an inhibitory monoclonal antibody-defined epitope on a malaria vaccine candidate antigen," Immunol. Lett., 23(4):305-309, Feb. 1, 1990.
Wagner et al., "Identification of an HLA-A*02 restricted immunogenic peptide derived from the cancer testis antigen HOM-MEL-40/SSX2," Cancer Immun., 3(18), pp. 1-15, Dec. 1, 2003.
Rammensee et al. (MHC Ligands and Peptide Motifs, Landes Bioscience, 1997, Austin, pp. 4-5, 7).
DiBrino et al. (PNAS USA, 1993, 90: 1508-1512).
DiBrino et al. (J. Immunol. 151: 5930-5935), 1993.
Anderson et al. (Cancer Immunol. Immunother. 1999, 48: 401-410).
Tourdot et al. (J. Immunol. 1997, 159: 2391-2398).
Geginat et al. (J. Immunol. 2001, 166: 1877-1884).
Rodkey. uth.tmc.edu/pathology/medic/immunology/Immuno/AgImmunogen07.pdf, 2010, pp. 1-25.
Alexander-Miller, M.A. et al., "Role of the antigen, CD8, and cytotoxic T lymphocyte (CTL) avidity in high dose antigen induction of apoptosis of effector CTL," The Journal of Experimental Medicine, 184:485-492, 1996.
Carter, Darrick et al., "Induction of cancer immunity by targeted hydrophobic ladders in the tumor antigen," FASEB Journal, Database Accession No. PREV200100264480, Mar. 8, 2001.
Dutoit, V. et al., "Heterogeneous T-cell response to MAGE-A10 (254-262): high avidity-specific cytolytic T lymphocytes show superior antitumour activity," Cancer Research, 61:5850-5856, 2001.
Supplemental European Search Report for International Application No. PCT/US03/06952, mailed on May 12, 2010, pp. 1-3.
Murray et al. (Proc. Ann. Meeting of the Amer. Assoc. for Canc. Res. 7/03, 44: 765-66), 2003.
Krebs et al. (Pharmaceutica Acta Helvetiae 73:173-81, 1998).
Rognan et al. (PNAS USA 1995, 92: 753-757).
Anderson et al., "Peptide priming of cytolytic activity to her-2 epitope 369-377 in healthy individuals," Clin. Cancer Res., 6:4192-4200, 2000.
Baker et al., "Conversion of a t cell antagonist into an agonist by repairing a defect in the tcr/peptide/mhc interface: implications for ter signaling," Immunity, 13:475-484, 2000.
Berman et al., "The Protein Data Bank," Nucleic Acids Research, 28:235-242, 2000.
Broome et al., "Expression of Bcl-2, Bcl-x, and Bax after T cell activation and IL-2 withdrawal," J. Immunol., 155:2311-7, 1995.
Brutlag et al., "Improved sensitivity of biological sequence database searches," Comput. Appl. Biosci., 6(3):237-245, 1990.
Castilleja et al., Induction of tumor-reactive CTL by C-side variants of the CTL epitope Her-2/neu ptotooncogene (369-377) selected by molecular modeling of the peptide: HLA-A2 complex, J. Immunol., 169(7):3545-3554, 2002.
Chicz and Urban, "Analysis of mhc-presented peptides: applications is autoimmunity and vaccine development," Immunol, Today, 15:155-160, 1994.
Chou and Fasman, "Conformational parameters for amino acids in helical, β-sheet and random coil regions calculated from proteins," Biochemistry, 13(2):211-222, 1974.
Chou and Fasman, "Prediction of protein conformation," Biochemistry, 13(2):222-245, 1974.
Ding et al., "Four a6-tcr/peptide/hla-a2 structures that generate very different t cell signals are nearly identical," Immunity, 11:45, 1999.
DiSomma et al., "TCR engagement regulates differential responsiveness of human memory t cells to fas (cd95)-mediated apoptosis," J. Immunol., 162:3851, 1999.
Eberl et al., "MHC class I H-2Kd-restricted antigenic peptides: additional constraints for the binding motif," Int. Immunol., 5(11):1489-1492, 1993.

(56) References Cited

OTHER PUBLICATIONS

Falk et al., "Allele-specific motifs revealed by sequencing of self-peptides eluted from mhc molecules," Nature, 351:290, 1991.

Fetrow and Bryant, "New programs for protein tertiary structure prediction," Biotechnology, 11(4); 479-484, 1993.

Fisk et al., "Mass-spectrometic analysis of naturally processed peptides recognized by ovarian tumor-associated cd8+ ctl," Int. J. Oncol., 10:159-169, 1997.

Fisk et al., "Identification of an immunodominant peptide of her-2/neu protooncogene recognized by ovarian tumor-specific cytotoxic t lymphocyte lines," J. Exp. Med., 181:2109-2117, 1995.

Garboczi et al., "Structure of the complex between human t-cell receptor, viral peptide and hla-a2," Nature, 384:134-141, 1996.

Geysen et al., "Use of peptide synthesis to probe viral antigens for epitopes to a resolution of as single amino acid," Proc. Natl. Acad. Sci., USA, 81:3998-4002, 1984.

Gillogly et al., "Induction of immunity to her-2 by ter directed variants of the ctl epitope e75," FASEB J., 14:A147.18, 2000.

Haskell-Luevano et al., "β-Methylation of the Phe7 and Trp9 melanotropin side chain pharmacophores affects ligand-receptor interactions and prolonged biological activity," J. Med. Chem., 40:2740-2749, 1997.

Hausman et al., "Peptide recognition by two hla-a2/tax11-19-specific t cell clones in relationship to their mhc/peptide/tcr crystal structures," J. Immunol., 162:5389, 1999.

Houghten et al., "A completely synthetic toxoid vaccine containing *Escheichia coli* heat-stable toxin and antigenic determinants of the heat-labile toxin b subunit," Infection and Immunity, 48:735-740, 1985.

Houghten, "General method of the rapid solied-phase synthesis of large numbers of peptides: specificity of antigen-antibody interaction at the level of individual amino acids," Proc. Natl. Acad. Sci., USA, 82:5131-5135, 1985.

Hruby et al., "Topographically designed analogues of [D-Pen, D-Pen5]enkephalin," J. Med. Chem., 34:1823-1830, 1991.

Jameson and Wolf, "The antigenic index: a novel algorithm for predicting antigenic determinants," Comput. Appl. Biosci., 4(1):181-186, 1988.

Kirchhoff et al., "TCR-mediated up-regulation of c-flipshort correlates with resistance toward cd95-mediated apoptosis by blocking death-inducing signaling activity," J. Immunol., 165:6293, 2000.

Knutson et al., "Immunization with a her-2/neu helper peptide vaccine generates her-2/neu cd8 t-cell immunity in cancer patients," J. Clin. Invest., 107:477, 2001.

Krammer et al., "CD95's deadly mission in the immune system," Nature, 407:789-796, 2000.

Lee et al., "Identification of activated tumor antigen-reactive cd8+ cells in healthy individuals," Oncol. Reports, 7:455-466, 2000.

Lu and Celis, "Use of two predicitve algorithms of the world wide web for the identification of tumor-reactive t-cell epitopes," Cancer Res., 60(18):5223-5227, 2000.

Madden et al., "The antigenic identity of peptide-mhc complexes: a comparison of the conformations of five viral peptides presented by hla-a2," Cell, 75:693-708, 1993.

Maden, "The three-dimensional structure of peptide-MHC complexes," Annu. Rev. Immunol., 13:587-622, 1995.

Mueller et al., "Differential regulation of bcl-2 and bcl-x by CD3, CD28, and the IL-2 receptor in cloned CD4+ helper T cells. A model for the long-term survival of memory cells," J. Immunol., 156:1764-71, 1996.

Parker et al., "Scheme for ranking potential hla-a2 binding peptides based on independent binding of individual peptide side-chains," J. Immunol., 153:163, 1994.

Peitsch et al., "Large-scale protein modelling and integration with the swiss-prot and swiss-2d page databases: the example of *Escherichia coli*," Electrophoresis, 18:498, 1997.

Rammensee et al., "SYFPEITHI: database for mhc ligands and peptide motifs," Immunogenetics, 50:213-219, 1999.

* cited by examiner

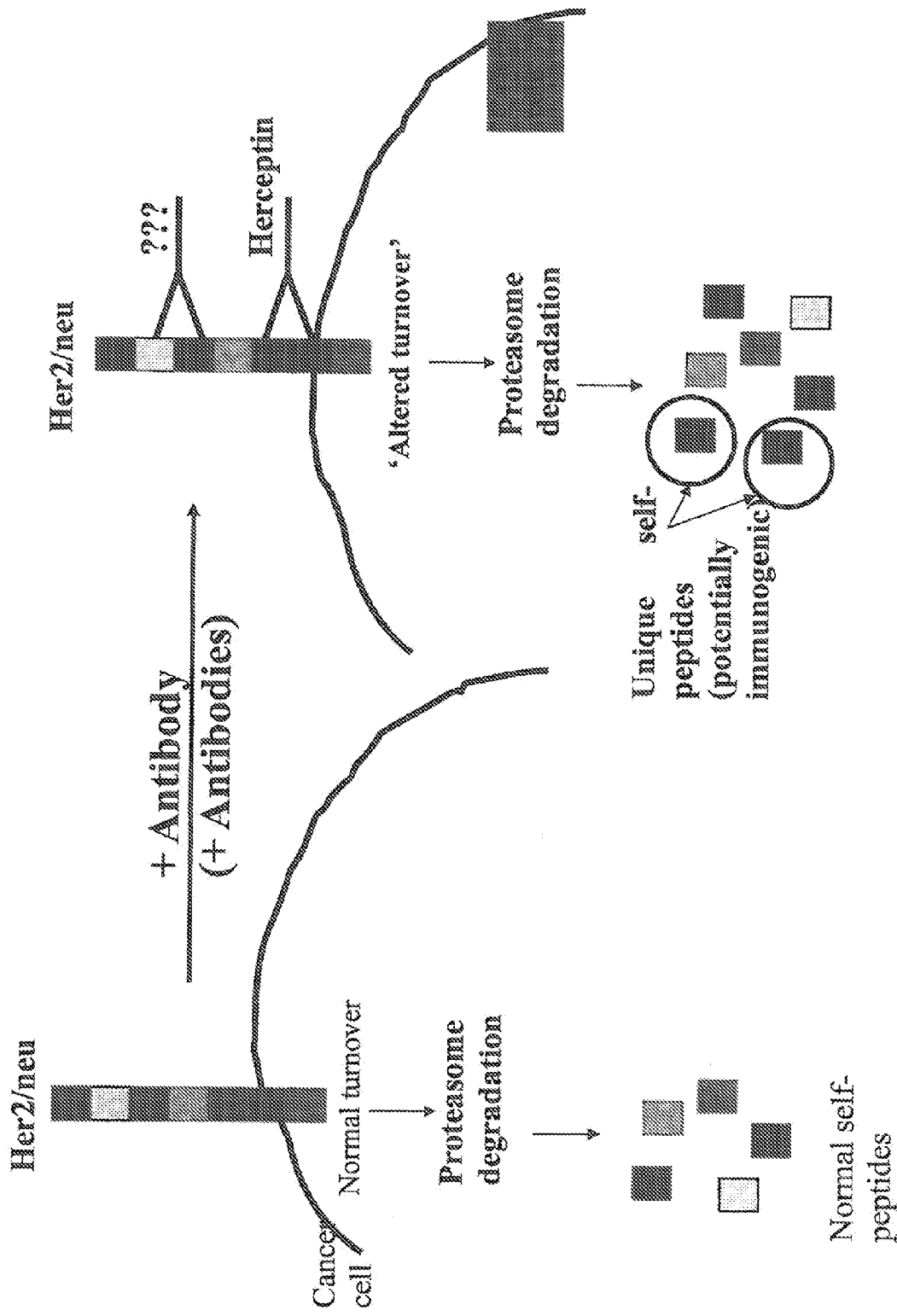

FIGURE 2

SEQ ID NO: 1 – Her2/neu SEQUENCE
1255 AA; 137909 MW; 39B9DFDA04DCF962 CRC64;

MELAALCRWG LLLALLPPGA ASTQVCTGTD MKLRLPASPE THLDMLRHLY QGCQVVQGNL
ELTYLPTNAS LSFLQDIQEV QGYVLIAHNQ VRQVPLQRLR IVRGTQLFED NYALAVLDNG
DPLNNTTPVT GASPGGLREL QLRSLTEILK GGVLIQRNPQ LCYQDTILWK DIFHKNNQLA
LTLIDTNRSR ACHPCSPMCK GSRCWGESSE DCQSLTRTVC AGGCARCKGP LPTDCCHEQC
AAGCTGPKHS DCLACLHFNH SGICELHCPA LVTYNTDTFE SMPNPEGRYT FGASCVTACP
YNYLSTDVGS CTLVCPLHNQ EVTAEDGTQR CEKCSKPCAR VCYGLGMEHL REVRAVTSAN
IQEFAGCKKI FGSLAFLPES FDGDPASNTA PLQPEQLQVF ETLEEITGYL YISAWPDSLP
DLSVFQNLQV IRGRILHNGA YSLTLQGLGI SWLGLRSLRE LGSGLALIHH NTHLCFVHTV
PWDQLFRNPH QALLHTANRP EDECVGEGLA CHQLCARGHC WGPGPTQCVN CSQFLRGQEC
VEECRVLQGL PREYVN    MPIWKFPDEE GACQPCPINC THSCVDLDDK GCPAEQRASP LTSIISAVVG
ILLVVVLGVV FGILIKRRQQ KIRKYTMRRL LQETELVEPL TPSGAMPNQA QMRILKETEL
RKVKVLGSGA FGTVYKGIWI PDGENVKIPV AIKVLRENTS PKANKEILDE AYVMAGVGSP
YVSRLLGICL TSTVQLVTQL MPYGCLLDHV RENRGRLGSQ DLLNWCMQIA KGMSYLEDVR
LVHRDLAARN VLVKSPNHVK ITDFGLARLL DIDETEYHAD GGKVPIKWMA LESILRRRFT
HQSDVWSYGV TVWELMTFGA KPYDGIPARE IPDLLEKGER LPQPPICTID VYMIMVKCWM
IDSECRPRFR ELVSEFSRMA RDPQRFVVIQ NEDLGPASPL DSTFYRSLLE DDDMGDLVDA
EEYLVPQQGF FCPDPAPGAG GMVHHRHRSS STRSGGGDLT LGLEPSEEEA PRSPLAPSEG
AGSDVFDGDL GMGAAKGLQS LPTHDPSPLQ RYSEDPTVPL PSETDGYVAP LTCSPQPEYV
NQPDVRPQPP SPREGPLPAA RPAGATLERP KTLSPGKNGV VKDVFAFGGA VENPEYLTPQ
GGAAPQPHPP PAFSPAFDNL YYWDQDPPER GAPPSTFKGT PTAENPEYLG LDVPV

SEQ ID NO: 2 – E75 Vaccine: KIFGSLAFL

SEQ ID NO: 3 – HER2 Herceptin binding region
PREYVNARHCLPCHPECQPQNGSVTCFGPEADQCVACAHYKDPPFCVARCPSG

FIGURE 3

HLA peptide motif search results

| User Parameters and Scoring Information | |
|---|---|
| method selected to limit number of results | explicit number |
| number of results requested | 20 |
| HLA molecule type selected | A_0201 |
| length selected for subsequences to be scored | 9 |
| echoing mode selected for input sequence | Y |
| echoing format | numbered lines |
| length of user's input peptide sequence | 53 |
| number of subsequence scores calculated | 45 |
| number of top-scoring subsequences reported back in scoring output table | 20 |

| | | Scoring Results | | |
|---|---|---|---|---|
| Rank | Start Position | Subsequence Residue Listing | Score (Estimate of Half Time of Disassociation of a Molecule Containing This Subsequence) | SEQ ID NO: |
| 1 | 27 | FGFEADQCV | 8.563 | 4 |
| 2 | 23 | SVTCFGFEA | 1.652 | 5 |
| 3 | 17 | CQPQNGSVT | 0.310 | 6 |
| 4 | 2 | RBYVNARHC | 0.062 | 7 |
| 5 | 38 | AHYKDPFFC | 0.061 | 8 |
| 6 | 5 | VNARHCLPC | 0.055 | 9 |
| 7 | 18 | QPQNGSVTC | 0.032 | 10 |
| 8 | 40 | YKDPFFCVA | 0.010 | 11 |

FIGURE 4

HLA peptide motif search results

| User Parameters and Scoring Information | |
|---|---|
| method selected to limit number of results | explicit number |
| number of results requested | 50 |
| HLA molecule type selected | A_0201 |
| length selected for subsequences to be scored | 9 |

Scoring Results

| Rank | Start Position | Subsequence Residue Listing | Score (Estimate of Half Time of Disassociation of a Molecule Containing This Subsequence) | SEQ ID NO: |
|---|---|---|---|---|
| 1 | 64 | PLPEADQCV | 131.751 | 12 |
| 2 | 46 | GILGFVFTL | 550.927 | 13 |
| 3 | 10 | KIFGSLAFL | 481.186 | 2 |
| 4 | 100 | IMDQVPPSV | 198.115 | 14 |
| 5 | 28 | RLLQETELV | 126.098 | 15 |
| 6 | 73 | FVPEADQCV | 114.778 | 16 |
| 14 | 82 | FGPEADQCV | 8.563 | 4 |
| 31 | 19 | IISAVVGIL | 0.612 | 17 |
| 32 | 37 | IVSAVVGIL | 0.390 | 18 |

FIGURE 5

| T2 Peptide-binding Assay | | |
|---|---|---|
| 25ug of peptide incubated with T2 cells | | |
| Levels of HLA-A2 were measured by flow cytometry | | |
| HLA-A2 levels are indicated as Mean Fluorescence Intensity units | | |
| | Expt 1 | Expt 2 |
| NP | 683 | 367 |
| Flu M | 1357 | 857 |
| E75 | 1151 | 474 |
| GP2 | 682 | 579 |
| 2G-577 | 1275 | 849 |
| 2L-577 | | 831 |
| 2V-577 | | 796 |

FIGURE 6

2G-577-stimulated cells can lyse tumor cells
Results expressed as % lysis

| PBMC 3 | Prostate Ca<br>LNCaP | Ovarian Ca<br>SKOV3-A2 | Breast Ca<br>MCF-7 |
|---|---|---|---|
| CM | 18 | 29 | 36 |
| E75 | 22 | 35 | 38 |
| 2G-577 | 36 | 38 | 50 |

| PBMC 7 | LNCaP | SKOV3-A2 | MCF-7 |
|---|---|---|---|
| CM | 22 | 37 | 38 |
| E75 | 32 | 38 | 30 |
| 2G-577 | 42 | 47 | 39 |

| PBMC 14 | LNCaP | SKOV3-A2 | MCF-7 |
|---|---|---|---|
| CM | 47 | 41 | 46 |
| E75 | 47 | 43 | 52 |
| 2G-577 | 52 | 50 | 52 |

FIGURE 7

Enhanced lysis of Herceptin-treated tumor targets by 2G, 2V, 2L-577-stimulated cells
Results expressed as % lysis

| PBMC 8 | MCF-7 | MCF7+10 Hercp | MCF7+ 50 Hercp | LNCaP | LNCaP+ 50 Hercp |
|---|---|---|---|---|---|
| CM | 46 | 49 | 53 | 15 | 46 |
| E75 | 47 | 51 | 53 | 30 | 47 |
| GP2 | 47 | 45 | 51 | 18 | 45 |
| 2G-577 | 35 | 48 | 52 | 27 | 48 |
| 2V-577 | 48 | 56 | 58 | 21 | 51 |
| 2L-577 | 50 | 54 | 50 | 26 | 52 |

| PBMC 10 | MCF-7 | MCF7+10 Hercp | MCF7+ 50 Hercp | LNCaP | LNCaP+ 50 Hercp |
|---|---|---|---|---|---|
| CM | 45 | 52 | 58 | 20 | 33 |
| E75 | 54 | 60 | 62 | 30 | 52 |
| GP2 | 51 | 58 | 66 | 35 | 41 |
| 2G-577 | 54 | 61 | 64 | 32 | 61 |
| 2V-577 | 57 | 64 | 64 | 27 | 85 |
| 2L-577 | 56 | 64 | 67 | 31 | 56 |

FIGURE 8

Enhanced lysis of Herceptin-treated tumor targets by 2G-577-stimulated cells from Breast Cancer patients. (Results expressed as % lysis)

| | Sample | MCF-7 | MCF7+50ug Hercp |
|---|---|---|---|
| BCa | NNV24 | 33 | 68 |
| BCa | NNV24 | 36 | 77 |
| BCa | B53V20 | 45 | 93 |
| BCa | B53V20 | 47 | 100 |
| Normal Donor | PBMC 3 | 32 | 80 |
| Normal Donor | PBMC 3 | 29 | 88 |

SEQUENCE LISTING

<160> NUMBER OF SEQ ID NOS: 18

<210> SEQ ID NO 1
<211> LENGTH: 1255
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

```
Met Glu Leu Ala Ala Leu Cys Arg Trp Gly Leu Leu Leu Ala Leu Leu
  1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350
```

```
Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
```

770             775             780
Leu Leu Gly Ile Cys Leu Thr Ser Thr Val Gln Leu Thr Gln Leu
785             790             795             800

Met Pro Tyr Gly Cys Leu Leu Asp His Val Arg Glu Asn Arg Gly Arg
            805             810             815

Leu Gly Ser Gln Asp Leu Leu Asn Trp Cys Met Gln Ile Ala Lys Gly
            820             825             830

Met Ser Tyr Leu Glu Asp Val Arg Leu Val His Arg Asp Leu Ala Ala
            835             840             845

Arg Asn Val Leu Val Lys Ser Pro Asn His Val Lys Ile Thr Asp Phe
            850             855             860

Gly Leu Ala Arg Leu Leu Asp Ile Asp Glu Thr Glu Tyr His Ala Asp
865             870             875             880

Gly Gly Lys Val Pro Ile Lys Trp Met Ala Leu Glu Ser Ile Leu Arg
            885             890             895

Arg Arg Phe Thr His Gln Ser Asp Val Trp Ser Tyr Gly Val Thr Val
            900             905             910

Trp Glu Leu Met Thr Phe Gly Ala Lys Pro Tyr Asp Gly Ile Pro Ala
            915             920             925

Arg Glu Ile Pro Asp Leu Leu Glu Lys Gly Glu Arg Leu Pro Gln Pro
            930             935             940

Pro Ile Cys Thr Ile Asp Val Tyr Met Ile Met Val Lys Cys Trp Met
945             950             955             960

Ile Asp Ser Glu Cys Arg Pro Arg Phe Arg Glu Leu Val Ser Glu Phe
            965             970             975

Ser Arg Met Ala Arg Asp Pro Gln Arg Phe Val Val Ile Gln Asn Glu
            980             985             990

Asp Leu Gly Pro Ala Ser Pro Leu Asp Ser Thr Phe Tyr Arg Ser Leu
            995             1000            1005

Leu Glu Asp Asp Asp Met Gly Asp Leu Val Asp Ala Glu Glu Tyr Leu
            1010            1015            1020

Val Pro Gln Gln Gly Phe Phe Cys Pro Asp Pro Ala Pro Gly Ala Gly
1025            1030            1035            1040

Gly Met Val His His Arg His Arg Ser Ser Ser Thr Arg Ser Gly Gly
            1045            1050            1055

Gly Asp Leu Thr Leu Gly Leu Glu Pro Ser Glu Glu Ala Pro Arg
            1060            1065            1070

Ser Pro Leu Ala Pro Ser Glu Gly Ala Gly Ser Asp Val Phe Asp Gly
            1075            1080            1085

Asp Leu Gly Met Gly Ala Ala Lys Gly Leu Gln Ser Leu Pro Thr His
            1090            1095            1100

Asp Pro Ser Pro Leu Gln Arg Tyr Ser Glu Asp Pro Thr Val Pro Leu
1105            1110            1115            1120

Pro Ser Glu Thr Asp Gly Tyr Val Ala Pro Leu Thr Cys Ser Pro Gln
            1125            1130            1135

Pro Glu Tyr Val Asn Gln Pro Asp Val Arg Pro Gln Pro Pro Ser Pro
            1140            1145            1150

Arg Glu Gly Pro Leu Pro Ala Ala Arg Pro Ala Gly Ala Thr Leu Glu
            1155            1160            1165

Arg Pro Lys Thr Leu Ser Pro Gly Lys Asn Gly Val Val Lys Asp Val
            1170            1175            1180

Phe Ala Phe Gly Gly Ala Val Glu Asn Pro Glu Tyr Leu Thr Pro Gln
1185            1190            1195            1200

```
Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
        1220                1225                1230

Pro Pro Ser Thr Phe Lys Gly Thr Pro Thr Ala Glu Asn Pro Glu Tyr
    1235                1240                1245

Leu Gly Leu Asp Val Pro Val
  1250                1255

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ile Phe Gly Ser Leu Ala Phe Leu
  1               5

<210> SEQ ID NO 3
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Arg Glu Tyr Val Asn Ala Arg His Cys Leu Pro Cys His Pro Glu
  1               5                  10                  15

Cys Gln Pro Gln Asn Gly Ser Val Thr Cys Phe Gly Pro Glu Ala Asp
              20                  25                  30

Gln Cys Val Ala Cys Ala His Tyr Lys Asp Pro Pro Phe Cys Val Ala
          35                  40                  45

Arg Cys Pro Ser Gly
      50

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Gly Pro Glu Ala Asp Gln Cys Val
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Val Thr Cys Phe Gly Pro Glu Ala
  1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Gln Pro Gln Asn Gly Ser Val Thr
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Glu Tyr Val Asn Ala Arg His Cys
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala His Tyr Lys Asp Pro Pro Phe Cys
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Asn Ala Arg His Cys Leu Pro Cys
  1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Pro Gln Asn Gly Ser Val Thr Cys
  1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Tyr Lys Asp Pro Pro Phe Cys Val Ala
  1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Leu Pro Glu Ala Asp Gln Cys Val
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ile Leu Gly Phe Val Phe Thr Leu
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Met Asp Gln Val Pro Phe Ser Val
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Leu Leu Gln Glu Thr Glu Leu Val
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Val Pro Glu Ala Asp Gln Cys Val
  1               5

<210> SEQ ID NO 17
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 17

Ile Ile Ser Ala Val Val Gly Ile Leu
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Val Ser Ala Val Val Gly Ile Leu
 1               5
```

TARGETED IDENTIFICATION OF IMMUNOGENIC PEPTIDES

REFERENCE TO RELATED APPLICATIONS

This application is a divisional of U.S. patent application Ser. No. 12/045,402, filed Mar. 10, 2008, which is a continuation of International Application No. PCT/US06/35171 filed Sep. 8, 2006, which claims priority to U.S. Provisional Application No. 60/714,865 filed Sep. 8, 2005, the entirety of which is hereby incorporated by reference.

RIGHTS IN THE INVENTION

This invention was made, in part, with support for the United States government and the United States government may have an interest in this invention.

BACKGROUND OF THE INVENTION

1. Field of the Invention

This invention, in the field of immunology/immunotherapy, vaccine discovery and development, relates generally to the identification of immunogenic peptides from regions of proteins and molecules that are involved in the binding interactions with polyclonal and monoclonal antibodies and other specific binding peptides/molecules. The present invention is directed to methods for identification and use of the peptides for preventing, suppressing and treating immune-related diseases. Specifically, the invention provides therapy that result in clinical improvement in cancer patients.

2. Description of the Background

Autoimmune diseases are characterized by an unwanted and unwarranted attack by the immune system on the tissues of the host. While the mechanism for progress of these diseases is not well understood, at least some of the details with respect to antigen presentation are known. It is thought that antigens, including autoantigens, are processed by antigen-presenting cells (APC), and the resulting fragments are then associated with one of the cell surface proteins encoded by the major histocompatibility complex (MHC). As a result, recognition of a peptide antigen is said to be MHC "restricted." When the MHC/antigen fragment complex binds to a complementary T cell receptor (TCR) on the surface of a T lymphocyte, activation and proliferation of the clone or sub-population of T cells result bearing that particular TCR. Once activated, T cells have the capacity to regulate other cells of the immune system which display the processed antigen and to destroy the cells or tissues which carry epitopes of the recognized antigen.

Antibody therapies in which antibodies are directed to MHC molecules and CD4 molecules have been generally successful in several animal models of autoimmunity. However, these approaches may be too nonspecific and potentially overly suppressive. This may be because 70% of T cells bear the CD4 marker and because all T cell-mediated responses and most antibody responses require MHC-associated antigen presentation.

A major difficulty with present approaches is that they require the use of complex biological preparations which do not comprise well-defined therapeutic agents. Such preparations suffer from complex production and maintenance requirements (e.g., the need for sterility and large quantities of medium for producing large number of "vaccine" T cells), and lack reproducibility from batch to batch. To be useful in humans, T cell "vaccine" preparations must be both autologous and individually specific. This means they must be uniquely tailored for each patient. Furthermore, the presence of additional antigens on the surface of such T cells may result in a broader, possibly detrimental, immune response not limited to the desired T cell clones (Offner et al., J. Neuroimmunol. 21:13-22 (1989).

There is a need, therefore, for agents and pharmaceutical compositions which have the properties of specificity for the targeted immune response. These agents and compositions should also have predictability in their selection, convenience and reproducibility of preparation, and sufficient definition in order to permit precise control of dosage.

An effective vaccine is capable of generating a long-lasting immunity while being relatively harmless to the recipient. Attenuated organisms and purified antigens from organisms have traditionally been used as vaccines. However, such agents often produce deleterious side effects or fail to protect against subsequent challenges. Because of the inherent difficulties in growing pathogenic organisms and producing effective vaccines from them, many viral, bacterial and parasitic diseases have no effective vaccine.

A further difficulty with the use of peptides as vaccines is that, in most instances, peptides alone are not good immunogens. It is a well known phenomenon that most immune responses to peptide antigens are T cell-dependent. Accordingly, "carrier" molecules have been attached to peptide antigens that bind, for example, to B cell surface immunoglobulin in order to generate a high affinity, IgG response. In other words, nonresponsiveness to peptide antigens may sometimes be overcome by attaching another peptide that induces helper T cell activity.

In general, peptides that induce helper T cell activity are generated by B cells from enzymatic digestion of native proteins internalized by way of an antibody receptor. These T cell stimulating peptides are then presented on the surface of the B cell in association with class II major histocompatibility complex (MHC) molecules. In a similar fashion, peptides that induce cytotoxic T cell activity may be generated by accessory cells, including B cells. These peptides are presented on the cell surface of accessory cells in association with class I MHC molecules. As used herein, the term "T cell stimulatory peptide" means any peptide which activates or stimulates T cells, including (but not limited to) helper T cells and/or cytotoxic T cells.

Peptides represent a promising approach to the production and design of vaccines. However, the difficulties in making peptides that induce the desired immune response have hampered their success. This includes the difficulties inherent in making peptides that closely mimic the native structure of antigenic determinants.

These antigenic determinants, or epitopes, of a protein antigen represent the sites that are recognized as binding sites by certain immune components such as antibodies or immunocompetent cells. While epitopes are defined only in a functional sense, i.e. by their ability to bind to antibodies or immunocompetent cells, there is a structural basis for their immunological activity.

Epitopes are classified as either being continuous and discontinuous. Discontinuous epitopes are composed of sequences of amino acids throughout an antigen and rely on the tertiary structure or folding of the protein to bring the sequences together and form the epitope. In contrast, continuous epitopes are linear peptide fragments of the antigen that are able to bind to antibodies raised against the intact antigen.

Many antigens have been studied as possible serum markers for different types of cancer because the serum concentration of the specific antigen may be an indication of the cancer stage in an untreated person. As such, it would be advantageous to develop immunological reagents that react with the antigen. More specifically, it would be advantageous to develop immunological reagents that react with the epitopes of the protein antigen.

Conventional methods using biochemical and biophysical properties have attempted to determine the location of probable peptide epitopes. These methods include a careful screening of a protein's primary structure, searching for critical turns, helices, and even the folding of the protein in the tertiary structure. Continuous epitopes are structurally less complicated and therefore may be easier to locate. However, the ability to predict the location, length and potency of the site is limited.

Various other methods have been used to identify and predict the location of continuous epitopes in proteins by analyzing certain features of their primary structure. For example, parameters such as hydrophilicity, accessibility and mobility of short segments of polypeptide chains have been correlated with the location of epitopes.

Hydrophilicity has been used as the basis for determining protein epitopes by analyzing an amino acid sequence in order to find the point of greatest local hydrophilicity. As discussed in U.S. Pat. No. 4,554,101, each amino acid is assigned a relative hydrophilicity numerical value which is then averaged according to local hydrophilicity so that the locations of the highest local average hydrophilicity values represent the locations of the continuous epitopes. However, this method does not provide any information as to the optimal length of the continuous epitope. Similarly, U.S. Pat. No. 6,780,598 B1 determines the immunopotency of an epitope by providing a ranking system delineating between dominant and subdominant epitopes.

Computer-driven algorithms have been devised to take advantage of the biochemical properties of amino acids in a protein sequence by sorting information to search for T cell epitopes. These algorithms have been used to search the amino acid sequence of a given protein for characteristics known to be common to immunogenic peptides. They can often locate regions that are likely to induce cellular immune response in vitro. Computer-driven algorithms can identify regions of proteins that contain epitopes which are less variable among geographic isolates, or regions of each geographic isolate's more variable proteins, or perform as a preliminary tool to evaluate the evolution of immune response to an individual's own quasi species.

Peptides presented in conjunction with class I MHC molecules are derived from foreign or self protein antigens that have been synthesized in the cytoplasm. Peptides presented with class II MHC molecules are usually derived from exogenous protein antigens. Peptides binding to class I molecules are usually shorter (about 8-10 amino acid residues) than those that bind to class II molecules (8 to greater than 20 residues).

Identification of T cell epitopes within protein antigens has traditionally been accomplished using a variety of methods. These include the use of whole and fragmented native or recombinant antigenic protein, as well as the more commonly employed "overlapping peptide" method for the identification of T cell epitopes within protein antigens which involves the synthesis of overlapping peptides spanning the entire sequence of a given protein. Peptides are then tested for their capacity to stimulate T cell cytotoxic or proliferation responses in vitro.

The overlapping peptide method is both cost and labor intensive. For example, to perform an assay using 15 amino acid long peptides overlapping by 5 amino acids spanning a given antigen of length n (a small subset of the possible 15-mers spanning the protein), one would need to construct and assay (n/5)–1 peptides. For most types of analyses, this number would be prohibitive.

Accordingly, a simple method to identify immunogenic peptides from regions of self-proteins and other proteins and molecules involved in binding interactions with polyclonal and monoclonal antibodies is needed.

DESCRIPTION OF THE FIGURES

FIG. 1 depicts one embodiment of the invention in which a unique immunogenic region of the HER-2/neu is identified.

FIG. 2 shows the Her2/neu sequence (SEQ ID NO: 1) and highlights the antibody-binding site of Herceptin to the Her2/neu protein. Also shown is the E75 vaccine sequence (SEQ ID NO: 2) and the Her2 loops binding to Herceptin (SEQ ID NO: 3).

FIG. 3 shows HLA peptide motif search results and scoring results for SEQ ID NOs: 4-11.

FIG. 4 shows amino acid substitutions for increased binding affinity of native peptide vaccine development. A table indicating HLA peptide motif search results, as well as the scoring results for SEQ ID NOs: 12-20 are included.

FIG. 5 depicts a T2 Peptide-binding assay, in which 25 μg of peptide were incubated with T2 cells, levels of HLA-A2 levels were measured by flow cytometry and are indicated as Mean Fluorescence Intensity units.

FIG. 6 is a table depicting an experiment looking at whether 2G-577- and E75-stimulated cells can lyse tumor cells, in prostate cancer, ovarian cancer, and breast cancer, with results expressed as % lysis.

FIG. 7 is a table showing enhanced lysis of Herceptin-treated tumor targets by E75, GP2, 2G-577, 2V-577, and 2L-577-stimulated cells, with results expressed as % lysis. These data suggest the benefit of combination therapy with Herceptin treatment and vaccine-induced T cell targeting for synergistic tumor cell killing.

FIG. 8 is a table showing enhanced lysis of Herceptin-treated tumor targets by 2G-577-stimulated cells from breast cancer patients, with results expressed as % lysis.

SUMMARY OF THE INVENTION

The invention overcomes the problems and disadvantages associated with current methods and provides tools and methods of generating an immune response in a patient in need thereof.

One embodiment of the invention is directed to a method for synthesizing an immunogenic peptide from a self-protein comprising the steps of identifying one or more peptide sequences of a self protein that are directly or indirectly involved with antibody-binding, subjecting the one or more peptide sequences to an algorithm that identifies sequences suspected of being immunogenic, screening all peptide fragments from the one or more peptide sequences, and identifying an immunogenic peptide of the protein fragment wherein the antibody-binding interaction is polyclonal or monoclonal. Further, a patient is treated with the immunogenic peptide to generate an immune response.

Another embodiment of the invention is directed to immunogenic peptides identified by the method described above.

Another embodiment of the invention is directed to an immunogenic peptide that produces an immune response to a self-protein.

Another embodiment is directed to a method of presenting epitopes for recognition by the immune system to generate an immune response comprising the steps of identifying a protein fragment that is recognized by a pool of unused and immunoreactive T cells, subjecting the protein fragment to an algorithm, identifying one or more specific sequences of the protein fragment that is immunogenic, synthesizing at least one immunogenic peptide corresponding to the sequence and treating a patient with the immunogenic peptide to generate an immune response. Further, an antibody that binds to the protein is generated.

Another embodiment of the invention is directed to immunogenic peptides identified by the method described above.

Another embodiment of the invention is directed to a vaccine comprising the immunogenic peptides described above.

Another embodiment of the invention is directed to a vaccine comprising antibodies that react with the immunogenic peptides described above.

Another embodiment of the invention is directed to a method of identifying a vaccine treatment comprising the steps of binding an antibody to a protein molecule forming a complex, subjecting the complex to proteasome digestion, obtaining digestion products comprising peptides, and identifying an immunogenic peptide sequence from the digestion products.

Another embodiment of the invention is directed to a method of identifying a patient-specific treatment comprising the steps of obtaining a pre-existing immuno-reactive precursor to said patient's AGIE/ABIE, culturing tumor cells obtained from said patient, incubating the cultured tumor cells that are reactive against generated antibodies, examining dataset responses in presence and absence of the generated antibodies and identifying the patient-specific immunogenic epitopes. This method may include the generation of antibodies that are reactive against self antigens, the generation of antibodies that are reactive against foreign antigens, and/or the generation of antibodies, once administered to said patient, that are therapeutic or prophylactic.

Another embodiment of the invention is directed to a method of identifying a vaccine treatment comprising the steps of binding an antibody to a protein molecule with a specific binding activity forming a complex, subjecting the complex to proteasome digestion, obtaining digestion producing comprising peptides, identifying an immunogenic peptide sequence from the digestion products.

Other embodiments and technical advantages of the invention are set forth below and may be apparent from the drawings and the description of the invention which follow, or may be learned from the practice of the invention.

DESCRIPTION OF THE INVENTION AND EXAMPLES

Treatments for complex diseases involving the immune system and immune responses caused by endogenous self antigens and/or foreign antigens that are involved in producing autoimmune antibody are extremely difficult to discover. Antigens involved with such diseases are either foreign or self antigens (or both). Administration of foreign antigens for passive immunization can result in serum sickness-like immune complex diseases. Also, reactive T cells capable of recognizing self peptides are typically deleted or processed and destroyed. These peptides, generated and displayed under normal and constitutive conditions are degraded by cell protein degradation machinery resulting in the absence of an immune response.

A simple method for identification of immunogenic regions of self-proteins and other proteins and molecules involved in the binding interactions with polyclonal and monoclonal antibodies has been surprisingly discovered. From this method, new and unique epitopes are generated that are presented in the presence of bound ligands, such as, preferably antibodies. Once these immunogenic regions are identified, vaccines comprising the antigen, modifications of the antigen, or antibodies specifically reactive to the antigen or the modified antigen can be prepared. Thus, the present invention makes vaccine peptide discovery manageable, and allows for the specific generation of unique immunogenic peptides from self-tumor associated proteins that can be induced or generated for specific expression in the presence of the antibody, allowing for vaccine and/or novel combination therapy.

The invention is described more fully herein and refers to many preferred embodiments. This invention, however, should not be construed as limited to those embodiments.

The proteasome is a multi-subunit complex with proteolytic cleavage activities that result in the generation of a wide variety of peptides from proteins. The susceptibility of a given protein to the proteolytic activities of the proteasome is dependent upon the various primary, secondary and tertiary structural and post-translational modifications that take place within the proteasome. These activities expose certain sequences or regions of the protein and not others, to the system.

In one embodiment of the invention, cancer cells are induced to express immunogenic peptides from unique or self tumor-specific antigens to stimulate anti-tumor immune responses for immunotherapy. Normally these peptides are not generated from self-proteins. Binding of antibodies (or other molecules) to the sites normally accessible and processed by proteasomes alters the pattern of accessibility and the resulting proteolytic cleavage pattern by the proteasome. Such alteration of the site results in generation of novel peptides that may be intrinsically immunogenic because they have not been previously expressed and displayed for the deletion of immuno-reactive T cells.

In one preferred embodiment, a unique immunogenic region of the HER-2/neu was identified. HER-2/neu is an over-expressed oncogenic protein. Conventional vaccine strategies, normally effective in immunizing patients, did not work with a "self-protein" such as HER-2/neu. Tolerance to self-proteins may only be directed to dominant epitopes of the protein and not the entire protein. Therefore, immunization to just a specific protein fragment, and not the entire protein, alleviates this problem. This specific protein fragment is located with in the sequence directly involved with antibody-binding interaction or in the proximity of that region.

After identifying this restricted, shorter peptide sequence, the sequence is subjected to algorithms to identify likely functionally active or target sequences or regions. Running algorithms on this segment, as opposed to the whole segment, provides a manageable set of peptides to test as candidates for vaccine development. In the past, computer-driven tests were run on the entire sequence consuming much time, money and effort. The algorithms searched the amino acid sequence provided for characteristic immune response in vitro. Regions of the proteins identified as containing epitopes may be useful as a vaccine.

Next, treatment of the tumor cells with the antibody against the identified peptide sequence was performed. Inducibility of the altered turnover and subsequent generation of the newly identified peptides only in the tumor cells and only in the presence of the antibody gave it a specific targeting and triggering feature that was controllable. See FIG. 1. An antibody booster can be given to increase the peptide-specific cytotoxic T cell response. In cases where the antibody already existed, discovery of the peptide only was sufficient for triggering the specific immune response.

The method to generate new and unique epitopes included the identification of immunogenic peptides from regions of proteins and molecules involved in the binding interactions with most any ligand including, but not limited to polyclonal and monoclonal antibodies, receptors, ligands and any molecule with high affinity to the antigen. These new epitopes were presented to antigen-processing cells in the presence of bound ligand. In certain cases, binding protected the epitope or a portion of the epitope revealing the immunogenic portion of the antigen. These immunogenic regions become new and uniquely enhanced targets for recognition by the immune system and for use in modulation of the immune responses for the treatment of disease states and immunotherapy either by themselves, an antibody vaccines, or when used in combination with other molecules or antibodies. These antibody-generated immunogenic epitopes (AGIE)/antibody-bound immunogenic epitopes (ABIE) were useful for stimulating immune response in cancer and infectious diseases. They can also suppress immune responses in autoimmune diseases and transplantation based upon the activity of the antibody in modulating the immune response in the direction of upregulation or down regulation.

Peptides varying in length including single chain antigen-binding polypeptides that can specifically interact, protect and/or modulate any given epitope such that it results in specifically protecting and/or enhancing the preservation and presentation of the epitope when subjected to the various proteolytic activities of the antigen processing machinery of the proteasome and immunoproteasome subunits and complexes.

Another embodiment of this invention comprises a combination of specific antibodies and/or treatment with other molecules that involve the same regions of the peptide sequences and targets unique populations of cells. This technology allows for the development of novel vaccines made of antibodies and/or antigen-binding fragments Fab or F(ab)'2-fragments bound to specific length peptides that contain immunogenic epitopes(s) of interest that are specifically processed and presented.

Specific epitopes of proteins may be protected, both intracellular and extracellular, that are normally destroyed by antigen processing machinery of proteasomes and immunoproteasomes by single chain antibodies and/or peptides that can specifically bind to selected site sequences so that these epitopes become novel targets that are developed as unique vaccines for the specific recognition of cancer cells. HSPs that are released during inflammatory processes perform similar activities and enhance immune responses because they were made to bind to many different peptide sequences non-covalently.

Another preferred embodiment of the invention is directed to a method for the identification of highly immunogenic peptides. These peptides are used to enhance or suppress immune responses from normal cell proteins that are not processed and presented naturally because of the constitutive destruction of these epitopes by the normal activities of the proteasome and immunoproteasome complexes. These peptides are used for generation for specific antibodies that bind and generate the novel presentation of these epitopes for recognition by the immune system.

In a preferred example, a large pool of immunoreactive T cells that are present or may be generated that are capable of reacting with these inert/naturally non-existent epitopes, but are not utilized and are considered "wasteful" because these epitopes are not being generated normally. This allows access to the pools of unused T cells for specifically directed therapeutic benefits. Again, computer-driven algorithms are run. Upon identification of the peptide sequences involved with antibody-binding interaction, these peptides are used to immunize animals and/or patients to generate specific antibodies that bind the protein and generate these novel peptides for subsequent immune recognition and response.

Another embodiment of the invention is directed to a direct method of binding antibody or antibodies to the protein molecules and/or polypeptide regions and subjecting these bound and unbound/native complexes to ex vivo or in vitro to all forms of the proteasome machinery. Proteolytic digestion or cleavage products are obtained to observe differential yield of peptides for use in vaccine development. However, there is a drawback to this method in that it is not fully representative of all "mechanisms and proteolytic activities" that may occur in vivo within the cell itself, thereby limiting application. Such an approach however, is useful for the proof of concept in systems where it provides clean reproducible and predictable results, e.g. using various individual components of proteasomes and combinations thereof and then observing peptide patterns by mass spectroscopy analysis. It is also useful for the definition of peptide patterns generated in the presence and/or absence of proteasome inhibitors with and without bound antibody or antibodies.

Another embodiment of the present invention involves application of this approach for identification of patient-specific treatment. Optimal antibody choices are made for the patient based upon patient's personal pre-existing immunoreactive precursors to the AGIE/ABIE. First, PBMC (peripheral blood mononuclear cells) are obtained from patient and culture in presence or absence of cytokines (eg IL-2, IL-7, and IL-15) in the presence of FCS (fetal calf serum) or autologous serum. After optimal culture and expansion during a set number of days, the cells are tested in cytotoxicity assays against tumor cell lines that have been pre-incubated in the presence and absence of specific antibodies or antibody combination(s). Datasets from responses seen specifically to presence of antibodies and those where individual antibodies do not yield a response, but the combinations that do are noted. The epitopes/vaccine peptides predicted or defined by the binding-sites of the antibodies are tested for fine reactivities in determination of which vaccines to use on patients.

Another embodiment of the invention is directed to identifying antigens that are not expressed on the cell surface or for parts of protein that are always cytoplasmic or for proteins that are completely intracellular/intranuclear or cytoplasmic (e.g. p53, telomerase, etc.). Methods for expressing the "modulating" antibody or antibodies as endogenous proteins, so that they are able to bind these proteins intracellularly and modulate their processing and presentation from within. The endogenous expression methods included recombinant DNA expression systems as well as viral/bacterial vector delivery and expression systems.

Another embodiment of the invention is directed to "shuttling" in the antibodies or single-chain antigen-binding fragment encapsulated within various delivery systems to include liposomes, micelles, nanoparticles and others.

Generation of "protective" or "suppressive" antibody preparations or combination capable of being administered passively for treatment of disease similar to the gamma-globulin shots were generated as polyclonal preps or as specific combinations of selected antibodies against one or more tumor or tissue specific antigens for that particular disease or condition.

The present invention is not restricted to HLA-A2 or class I peptides because one or more longer-length peptides from a known region or sequence can be used for the generation of AGIE/ABIE by the antibody or antibodies in question. The benefit is not having to be restricted by only specific or limited HLA types (Class I and II) in terms of patients that can be treated. Furthermore, although the majority of Class I and Class II peptides are derived from the processing of endogenous and exogenous proteins respectively, the well described and accepted mechanisms of "cross-presentation" allows for the presentation of all sources or peptides on both classes of MHC molecules.

In another embodiment of the invention, the invention is used for identifying inducible vaccine responses by "discovering" the MAb/s that will generate AGIE/ABIE. This is achieved by first screening 10-mer or 20-mer consecutive or overlapping peptides from antigen for the highest precursor T-cell responses present in cancer and/or normal individuals. These "ultra-immunogenic" peptides are then used for generation of MAb in mice. These MAbs are then tested for ability to generate AGIE/ABIE specific responses in MAb-treated targets. MAbs that are promising are then humanized for therapeutic purposes. To ensure involvement of T cell specific immune responses the promising Fab' fragments are first used to eliminate purely antibody-dependent cell-mediated cytotoxicity (ADCC)-mediated activity.

Another way of specifically identifying peptides capable of generating antibodies that induce AGIE/ABIE that are most protective is by the method of screening serum sample from high-risk cancer individuals (those with family history of cancer, e.g. smokers who do and do not get lung cancer, patients who are 'cured') who do and do not develop cancer (or from progressor vs non-progressors in the case of AIDS) to look for Ab responses against the overlapping peptides from specific well characterized or defined tumor antigens (HER2/neu, prostate specific antigen or PSA, prostate specific membrane antigen or PSMA, Tyrosinase, melanoma Ags, etc.) that are present in the protected individuals or present in fully recovered/cured cancer patients. Based on the specific Ab responses that are found to be uniquely present or predominantly present in the 'protected' individuals, peptides are targeted for generation or 'discovering' of MAb that generated AGIE/ABIE. All descriptions herein were done for both Class I and Class II epitopes and responses.

In a preferred embodiment, data of appropriate combinations of antibodies from published sources with well documented 'pre-existing' corresponding CD4-helper and CD8 CTL-specific responses is used for developing a vaccine for the AIDS virus and other immunotherapy treatment using the approach from the present invention. The HIV Molecular Immunology Database provided by the National Institute of Allergy and Infectious Diseases at www.hiv.lanl.gov offers a current comprehensive listing of defined HIV epitopes. The website also includes the exact epitope and binding site of all known monoclonal and polyclonal antibodies to the protein sequences as well as neutralization activity.

The present invention provides enhanced lytic activity of antibody-treated tumor cells by vaccines identified from the binding sites of these antibodies. The present invention also provides a novel indication for antibodies already in clinical use for cancer treatment as combination therapy furthering development of vaccine treatment discovery.

EXAMPLE

The binding of trastuzumab (Herceptin) to HER2/neu for the development of novel vaccines against HER2/neu-expressing tumors was studied. The Ab-binding site of trastuzumab (Tz) was analyzed for peptides that bind HLA-A2 and A3. A peptide Her577 (aa: 577-585) within the Ab-binding site on HER2/neu was identified, synthesized and tested. T2 HLA-stabilization assays were performed to confirm HLA-A2 binding activity of Her577 by flow cytometry. PBMC from 9 healthy donors were stimulated with Her577 and tested in $^{51}$Cr-release cytotoxicity (CTX) assays against 3 HER2/neu-expressing tumor cell lines. Her577-stimulated PBMC from 5 HLA-A2$^+$ healthy donors were also tested in CTX with HER2/neu$^+$ targets pre-treated with Tz. Simultaneous experiments were done with E75 and GP2, two other immunogenic peptides from HER2/neu.

The Her577 peptide bound HLA-A2 comparable to E75 and GP2 with mean fluorescence intensity values of 1275, 1151 and 682, respectively. The average specific CTX by Her577-stimulated cytotoxic T lymphocytes (CTL) against LNCaP, SKOV-3 and MCF-7 tumor cells was found to be similar to CTX achieved with E75- and GP2-stimulated CTL (% lysis; Table 1).

TABLE 1

| | LNCaP (HLA-A2$^+$) (n = 2) | SKOV-3 (HLA-A3$^+$) (n = 2) | MCF-7 (HLA-A2$^+$) (n = 5) |
|---|---|---|---|
| Her577 | 30 ± 3 | 49 ± 28 | 45 ± 3 |
| E75 | 30 ± 1 | 51 ± 20 | 51 ± 4 |
| GP2 | 26 ± 9 | 46 ± 5 | 48 ± 1 |

Pre-treatment with Tz at 50 μg/ml for 24 h increased specific CTX by Her577-stimulated CTL versus untreated MCF-7, SKOV-3 and LNCaP by 16%, 47% and 83%, respectively (P=0.19). A dose-dependent incremental increase in CTX against each tumor cell line was seen with 10 and 50 μg/ml doses of Tz.

It can be concluded that Her577 is a newly described T cell-epitope from HER2/neu identified by using a novel method for the discovery of immunogenic peptide(s) for vaccine development by assessing the binding site of Tz. There is a potential for combination immunotherapy with therapeutic Ab and unique peptide vaccines derived from the Ab-binding site.

Other embodiments and uses of the invention will be apparent to those skilled in the art from consideration of the specification and practice of the invention disclosed herein. All references cited herein, including all patents and publications that are cited for any reason, including U.S. Provisional Application No. 60/714,865, on which priority is based, are specifically and entirely incorporated by reference. The specification and examples should be considered exemplary only with the true scope and spirit of the invention embodied within the following claims.

The invention claimed is:

1. A method for treating a patient with a cancer expressing HER2/neu comprising administering to the patient an immunotherapy consisting of,
   (a) a therapeutically effective amount of trastuzumab; and
   (b) a therapeutically effective amount of a peptide vaccine comprising a HER2/neu peptide antigen consisting of the amino acid sequence of SEQ ID NO: 2, as the sole peptide antigen in the vaccine.

2. The method of claim 1, wherein administration of trazstuzumab and the peptide vaccine have a synergistic effect on the patient.

3. The method of claim 1, wherein the patient is a breast cancer patient.

4. The method of claim 1, wherein the cancer is selected from the group consisting of prostate cancer, ovarian cancer and breast cancer.

5. The method of claim 1, wherein the peptide vaccine is administered after administration of the trastuzumab.

6. A method of inducing an immune response to HER2/neu in a patient with a cancer expressing HER2/neu, the method consisting of administering a therapeutically effective amount of,
   (a) trastuzumab; and
   (b) a peptide vaccine comprising a HER2/neu peptide antigen consisting of the amino acid sequence of SEQ ID NO: 2, as the sole peptide antigen in the vaccine.

7. The method of claim 6, wherein the peptide vaccine is administered after administration of the trastuzumab.

8. The method of claim 6, wherein the cancer is selected from the group consisting of prostate cancer, ovarian cancer and breast cancer.

9. The method of claim 8, wherein the cancer is breast cancer.

* * * * *